United States Patent [19]

Strohmaier et al.

[11] 4,359,317
[45] Nov. 16, 1982

[54] ARRANGEMENT FOR CONVEYING A STERILE LIQUID TO A SURGICAL OPERATING LOCATION

[75] Inventors: Ernst Strohmaier, Bd. Schussenried; Hans Scheicher, Munich; Eugen Eibofner, Biberach, all of Fed. Rep. of Germany

[73] Assignee: Kaltenbach & Voight GmbH & Co., Biberach, Fed. Rep. of Germany

[21] Appl. No.: 212,513

[22] Filed: Dec. 3, 1980

[30] Foreign Application Priority Data

Jun. 12, 1979 [DE] Fed. Rep. of Germany ....... 2949142

[51] Int. Cl.³ .............................. A61C 1/10; A61C 1/12
[52] U.S. Cl. ......................................... 433/85; 433/87
[58] Field of Search ..................... 433/80, 84, 85, 86, 433/87

[56] References Cited

FOREIGN PATENT DOCUMENTS 575814  8/1924  France ................................. 433/84

Primary Examiner—Robert Peshock
Attorney, Agent, or Firm—Scully, Scott, Murphy & Presser

[57] ABSTRACT

An arrangement for the conveyance of a sterile liquid to a surgical treating or operating location, consisting of a liquid receptacle containing the sterile liquid, from which there can be dispensed the sterile liquid under the effect of pressure through a dispensing conduit from the dispensing end thereof, wherein the dispensing conduit is provided with a valve arrangement for regulating the throughflow.

5 Claims, 9 Drawing Figures

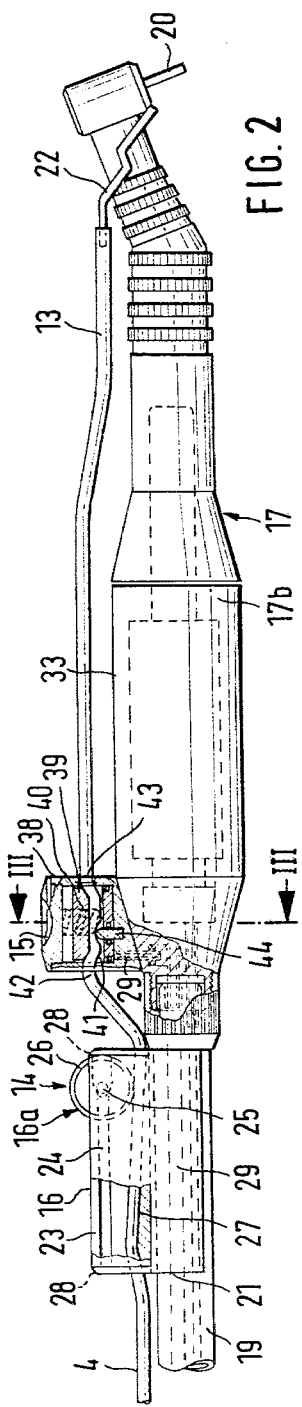
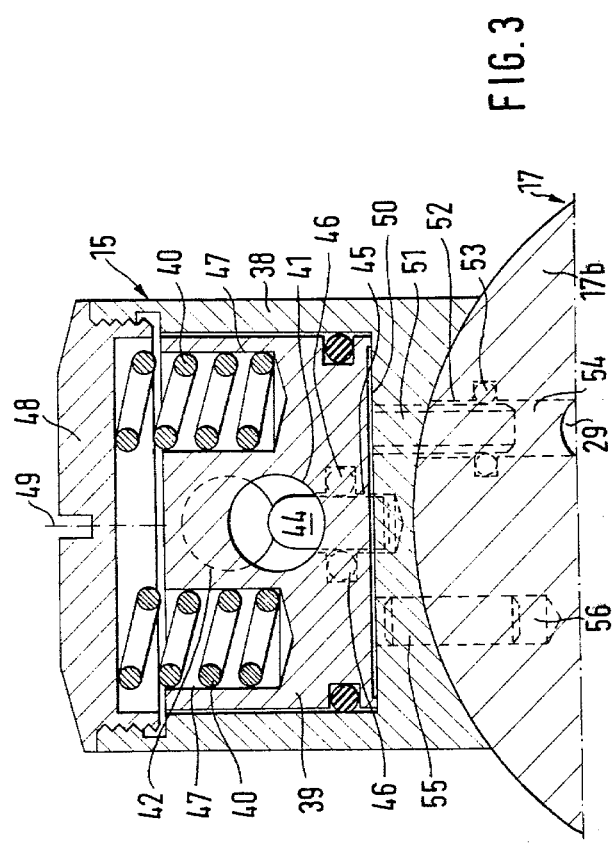

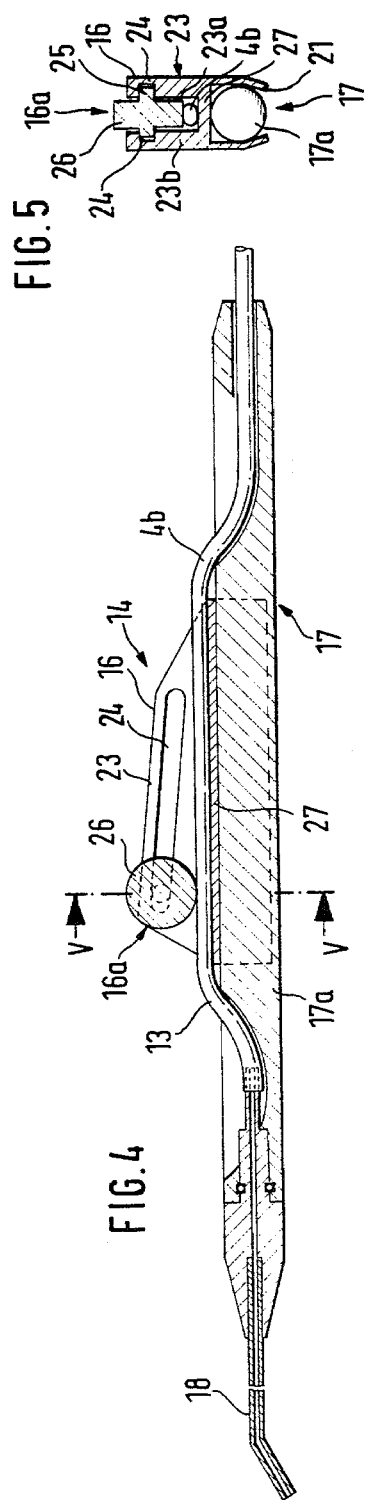

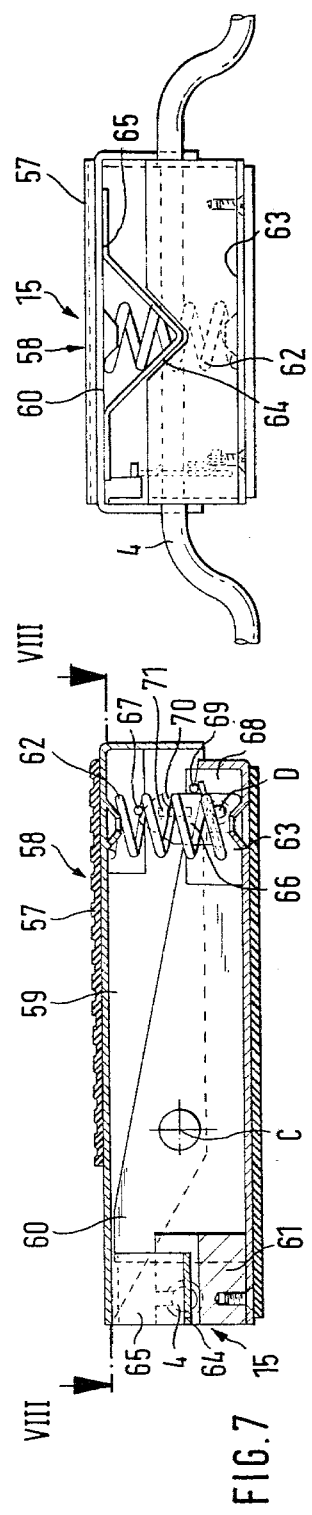
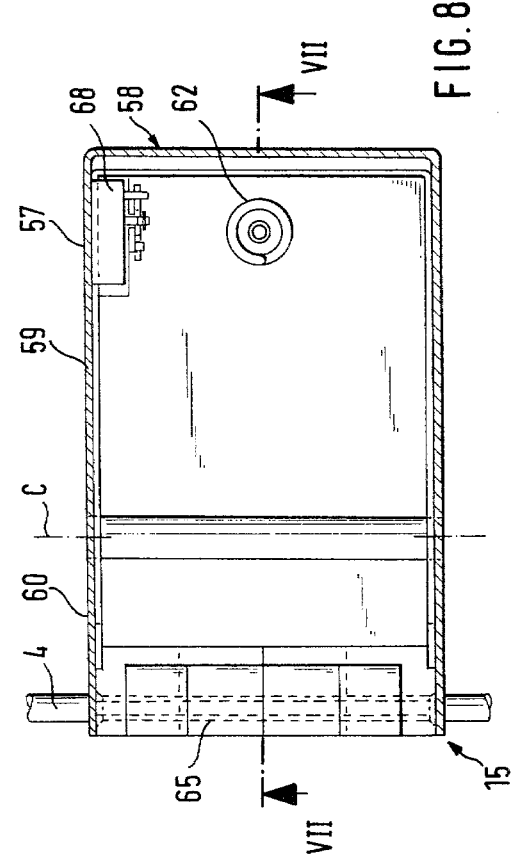

ARRANGEMENT FOR CONVEYING A STERILE LIQUID TO A SURGICAL OPERATING LOCATION

BACKGROUND OF THE INVENTION

1. Field of the Invention

The present invention relates to an arrangement for the conveyance of a sterile liquid to a surgical treating or operating location, consisting of a liquid receptacle containing the sterile liquid, from which there can be dispensed the sterile liquid under the effect of pressure through dispensing conduit from the dispensing end thereof, wherein the dispensing conduit is provided with a valve arrangement for regulating the throughflow.

The infeed of sterile or aseptic liquids can become necessary for transfusions, as well as for the cooling of the work tools, in effect for maintaining moist and the cooling of the treatment location for surgical, in particular, bone jaw surgical or orthopedic applications, such as for stress-relieving treatments on the bone or on the tooth, for example, during drilling, milling or sawing, and also during special operations such as grinding and polishing, especially in the dental treatment technology. The sterile or, in effect, aseptic liquid can be a physiological common salt solution (NaCl), an infusion liquid, a medicated solution or the like. The liquid receptacle can be formed by a commercially available infusion bottle from a plastic material. The dispensing conduit is preferably constructed from a flexible hose of an elastic material.

2. Discussion of the Prior Art

The inventive liquid receptacle, for example, pursuant to German Petty Patent No. 70 31 511 can encompass a tubularly-shaped closed receptacle of a rigid material in which there is arranged an axially slidable displacement piston which can be subjected to power from both sides, which sealingly divides the receptacle chamber into a fluid chamber which receives the sterile fluid and forms the actual liquid receptacle-forming chamber, and into a dosing chamber which means by means of a pressure medium conduit which is connected to a pressure medium source and receives the pressurized medium, serves for quantity dosage of the sterile liquid.

In the arrangement which has become known through the German Petty Patent No. 70 31 511, the pressurized medium conduit has a foot control switch associated therewith as a valve arrangement for the regulation of the throughflow. The quantity of the sterile liquid which is to be dispensed is hereby dosed through variation of the air pressure. This, however, is an indirect and thereby delayed regulation of the dispensed liquid quantity and, at the dispensing end of the dispensing conduit, can lead to irregularities with respect to the agressing sterile liquid, which can be deleterious or at least uncomfortable for the treatment location of the human body.

The inventive liquid receptacle, in accordance with German Pat. No. 2,258,069 can also evidence elastically deformable walls and be arranged in a sealingly closable outer receptacle having rigid walls wherein, in a similar manner as in the previously described known construction, the liquid receptacle possesses a liquid connection for connecting a dispensing conduit which, however, in this instance traverses the outer receptacle, and whereby the outer receptacle also includes a pressure connector for the connection of a pressurized medium source.

Also in the arrangement pursuant to German Pat. No. 22 58 069 is the valve arrangement associated with the pressure conduit so that, through the herein required indirect regulation, there occur the same disadvantages as in the previously described known type of construction.

Furthermore, from the prospectus DRUCKMATIK LF 76 there has become known an arrangement of the above mentioned type in which the arrangement and construction of liquid receptacle and outer container is the same as in the arrangement pursuant to German Pat. No. 22 58 069.

However, the arrangement which has become known through the mentioned prospectus corresponds to the above-mentioned art since the valve arrangement is not associated with the pressurized medium conduit but with the dispensing conduit so that there is effected a direction regulation. Nevertheless, even in this known arrangement the regulation of the throughflow is delayed since, in essence, the valve arrangement, with the formation of a further conveying path up to the dispensing end, is found in the region of the receptacle-sided end of the dispensing conduit, which brings along the additional disadvantage in that the operator, for instance, a dentist, can only with difficulty reach a valve which is actuated by hand so as to cause a further delay.

SUMMARY OF THE INVENTION

The invention, accordingly, has as its object to provide an arrangement of the above-mentioned type in which upon actuation of the applicable valve there is obtained the desired result practically without any delay, in essence, the stopping and starting of the outflow from the dispensing end, or the reduction or increase in the outerflow quantity for each unit of time.

The advantages which are achieved by the invention can be essentially seen in that through the immediate proximity of the valve arrangement at the dispensing end of the dispensing conduit there are required by the operator only extremely short paths or motion for the actuation of the valve arrangement which, in this manner, is comfortably reached with the hand or even only with one finger of the hand that otherwise holds the dispensing end so as to be brought back. Moreover, the above mentioned immediate proximity has the effect that the desired result of the valve actuation is achieved practically instantaneously or, in essence, without delay.

BRIEF DESCRIPTION OF THE DRAWINGS

Reference may now be had to the detailed description of the preferred embodiments of the invention, taken in conjunction with the accompanying drawings; in which:

FIG. 2 shows a dispensing end of the dispensing conduit, in an enlarged representation, in a sideview and in section FIG. 3 is a section taken along line III—III in FIG. 2;

FIG. 4 illustrates an embodiment which is modified with respect to that shown in FIG. 2;

FIG. 5 is a section taken along line V—V in FIG. 4;

FIG. 6 is a top plan view of the embodiment of FIG. 4;

FIG. 7 is the foot actuator of the arrangement illustrated in FIG. 1 in phantom lines in a section taken along line VII—VII in FIG. 8;

FIG. 8 is the foot actuator in a section taken along line VIII—VIII in FIG. 7; and FIG. 9 shows the foot actuator pursuant to FIGS. 7 and 8 in cross-section.

DETAILED DESCRIPTION

Figure 1:
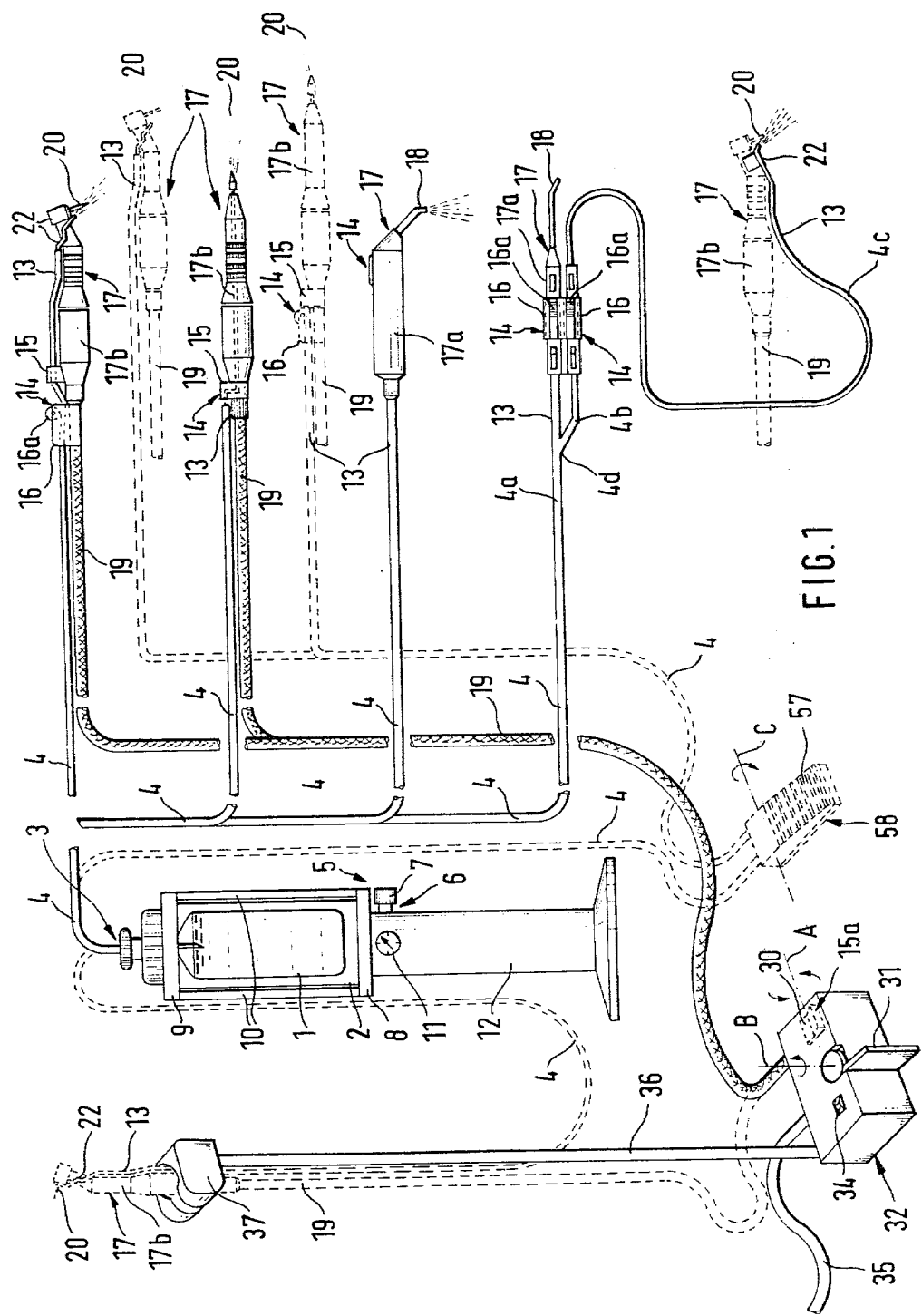
FIG. 1 illustrates the arrangement in a schematic representation with a plurality of capability for the arrangement, such as construction of the dispensing end of the dispensing conduit.

The arrangement for the supply of sterile or aseptic fluid to a surgical treatment or operating location, in the embodiment illustrated in FIG. 1, consists of an inner liquid receptacle 1 which contains the mentioned liquid and which has elastically deformable walls, which is arranged within an outer container 2 constructed of sealably closable rigid walls of transparent material, for example, glass or plastic. The mentioned transparency renders it possible that the remaining quantity and, occassionally, the condition of the sterile liquid can be observed. For example, there are sterile liquids which when in a cloudy condition may no longer be utilized.

The liquid or fluid receptacle 1 is provided with a fluid connector 3 for connection to a dispensing conduit 4 which traverses the outer container 2, and the outer container 2 with a pressure connector 5 for connection to a pressurized medium source 6.

The pressure connector 5, pursuant to FIG. 1 can be constructed as a screw cover 7 projecting sideways into the atmosphere, in which a compressed gas cartridge (not shown) can be utilized as the pressurized medium source 6 with its penetrable end facing in a direction towards a connecting passageway (not shown) with an opening having a hollow penetrating mandrel leading into the outer container 2 connected to the pressure connector 5, however, in a not illustrated manner, there can also be a pressure medium conduit which communicates with a pressurized medium source.

As the pressurized medium there can be basically utilized a pressurized liquid or compressed gas. The utilization of pressurized gas, in particular, hydrogen or compressed air, is however most suitable.

The two end walls 8 and 9 of the, for the remainder cylindrical, outer container 2 are held against each other by tension rods 10.

The arrangement, as illustrated in FIG. 1 can be stood on the floor by means of an upright column 12 which includes a monometer 11, or can find application with the end wall 8 upwardly extending, for example, as a suspended apparatus or any suitable intermediate position, for example, lying down.

The dispensing conduit 4 from dispensing end 13 of which the sterile liquid exiting from the fluid receptacle 1 under the influence of pressure acting on the fluid receptacle 1 by subjecting the outer container 2 with pressurized medium, is provided with a valve arrangement 14 for regulating the liquid throughflow. The valve arrangement 14 is provided in the region of the dispensing end 13 of the dispensing conduit 4 and consists of an on-off valve 15 and a regulating valve 16 which varies the throughflow quantity per unit of time, respectively, pressure varying.

As illustrated in FIGS. 1 through 6, the dispensing end 13 of the dispensing conduit 4 is arranged on a preferably cylindrical handpiece 17. The handpiece 17, pursuant to FIGS. 1 and 4, can be constructed at one of its ends as a spray nozzle 18 containing medical, and particularly dental spray handpiece 17a, wherein the dispensing conduit is introduced at the other end of the spray handpiece 17a, and the valve arrangement 14 is arranged in or on the spray handpiece 17a. The valve hand grips or the like are hereby designated with 15a, 16a. The handpiece 17, pursuant to FIGS. 1 and 2, can also be constructed as connected with one of its ends to a supply hose 19 and at its other end have a treatment work tool 20, for example, a drill incorporating medical, particularly dental treatment handpiece 17b, whereby the dispensing conduit 4 is positioned interiorly or, as illustrated exteriorly on the handpiece 17b, and the valve arrangement 14 is fastened to the supply hose 19 or to the handpiece 17b.

The valves 15, 16 of the valve arrangement 14, as illustrated in FIG. 2 for the regulating valve 16, are for instance with the aid of an elastic clamp 21 detachably connected with the supply hose 19, or with the treatment handpiece 17b, or as illustrated in FIG. 5, with the spray handpiece 17a. In lieu of the connection with the mentioned clamp, the valves 15, 16 can also be connected through adhesion with the handpiece 17. From FIGS. 1 and 2 there can be ascertained that the treatment handpiece 17b, in the region of the end towards the work tool, externally evidences a spray passageway 22 to which there is connected the dispensing end 13 of the dispensing conduit 4.

Pursuant to FIGS. 1 and 6, the dispensing conduit 4 can be constructed so as to fork into two branch conduits 4a, 4b, of which one leads to a medical spray handpiece 17a and the other, through a short extension conduit 4c, to a medical treatment handpiece 17b, as may be ascertained from the representation in the lower left in FIG. 1. Hereby the spray handpiece 17a, as viewed in the flow direction of the sterile liquid, is connected shortly behind the fork 4d to its branch conduit 4e.

As may be further ascertained from FIGS. 1 and 6, the valve arrangement 14 of the spray handpiece 17a and the valve arrangement 14 of the treatment handpiece 17b can be separately actuatable, but located constructively united on the spray end pieces 17a and suitably detachable. Hereby, it is possible that an assistant, for example, a dental assistant, can with the aid of the spray handpiece 17a through actuation of the lower handgrip 16a as shown in FIGS. 6, introduce sterile liquid for example, for the rinsing and removing of small fragments or chips to the operating area and, concurrently with the aid of the upper handgrip 16a as shown in FIG. 6 can regulate the supply of the sterile liquid to the treatment handpiece which is utilized by the treating person, for example, for drilling.

In the foregoing instance it is often sufficient when the two valve arrangements 14 presently encompass only a single regulating valve 16.

As is illustrated in FIGS. 2 through 9, the valves 15, 16 of the valve arrangement 14 are presently constructed as the clamping or squeezing valves which act from the exterior of the dispensing conduit 4 which is constructed as an elastic hose.

Hereby, pursuant to FIGS. 2, 4, 5 and 6, the regulating valve 16 of the valve arrangement 14 consists of a rail 23 which is U-shaped in cross-section. At the inside of its two side walls 23a, 23b, the rail 23 is provided with mutually oppositely located guide grooves 24 for the ends of a roll shaft 25 of a clamping wheel 26 which forms the valve handgrip 16a, whereby the bottom 27 of the U-shaped rail 23 and the guide grooves 24 are inclined towards each other, and between the above mentioned bottom and the clamping wheel there runs the dispensing conduit 4 which extends along the rail. At the ends of the rail 23 the U cross-section can be arranged to a transverse lock 28 which extends to rectanguar cross-section wherein the dispensing conduit 4 extends through the rectangular cross-sections. At the rotation of the clamping wheel 26 this will move, in accordance with the direction of rotation, in one or the other direction so that an increase or, respectively, a decrease in the squeezing together of the dispensing conduit 4 which is formed as an elastic hose, and thus results in an increased or in a reduced dispensing of sterile liquid from the dispensing end 13. The clamping wheel 26 can be provided with serrations about its pheriphery for improved manipulation thereof.

FIG. 2 illustrates an embodiment in which the clamping valve which forms the on-off valve 15 is controlled by compressed-air, and for this purpose is connected with a compressed-air control conduit 29, compare also with FIG. 3. The compressed-air control conduit 29 suitably extends in the supply hose 19 which leads to a dental treatment handpiece 17b and is connected with a foot switch 30 (compare with FIG. 1) which activates and deactivates the compressed-air supply. The foot switch 30, which is constructed as a rocker-type switch, and which forms the actuating element 15a for the on-off valve 15 is presently tiltable about the axis A in the sense of the two associated arrows into the on or off positions. The foot switch 39 is constructively united with a foot regulator 31 constructed as a pivot lever pivotable about an axis B in the sense of the associated arrows, and which regulates the rotational speed and-/or the direction of rotation of the work tool 20 of a treatment handpiece 17b. The common switch housing is designated with 32 and at its upper surface additionally possesses a foot-actuatable on-off switch 34 associated with, for example, the electric drive motor 33 (FIG. 2) of the handpiece 17b.

Leading to the foot switch housing 32 is a main medium supply conduit 35 meeting thereto, whereas the supply hoses 19 leads to the treatment handpieces 17b from the foot switch housing 32. The switch housing 32 also possesses an, for example, 1 meter upwardly extending support rod 36 on the upper end of which there is arranged a stiff upright-like retaining element 37 for a removable handpiece 17b. The valve arrangement 14 which is associated with the treatment handpiece 17b is covered by the retaining element 37.

As may be ascertained from FIGS. 2 and 3, the clamping valve which encompasses the on-off valve 15 includes in a cylindrical housing 38 a reciprocable piston 39 which acts on the dispensing conduit 4, whose one side is subjected, opposite the effect of at least one spring 40, to compressed air which emanates from the compressed-air control conduit 29 whereby, at a switched off compressed-air infeed, the piston 39 will act under the effect of the spring 40 on the elastic dispensing conduit 4 in the sense of the closing thereof. In the illustrated instance, pursuant to FIG. 3 there are provided two springs 40.

The freely moveable or overhung positioned piston 39 possesses a throughbore 41 extending transverse to its direction of movement through which there extends by means of inlet and outlet apertures 42, 43 formed in the wall of the cylinder housing 38 the dispensing conduit 34, whereby there is arranged, on the compressed air-expose side of the piston 39, a fixed clamping pin 44 in the cylinder housing 38, which extends through a recess 45 in the piston 39 into the throughbore 41 and serves as a clamping abutment at the closing of the dispensing conduit 4. Hereby, for the frictionless support of the piston 39 and accordingly, to achieve a still more rapid response of the on-off valve 15 in the wall of the through-recess 45 of the piston 39, there are supported ball bearings 46 which are located against the clamping pin 44.

The two springs 40 are constructed as helical compression springs and are arranged on the side of piston 39 opposite the side subjected to the compressed air. For the retention of the springs 40, the piston 39 possesses an inserting blind hole 47 for each spring. At the opposite end distal to the blind hole 47, the springs 40 are positioned against a closure cover 48 which, as shown in FIG. 3, is screwed onto the upper end of the cylinder housing 38 which externally evidences a slot 49 for engagement by a screwdriver or the like. Through rotation of the closure cover 48 there can be varied the spring force of the springs 40.

Pursuant to FIG. 3, a control air supply passageway 51 leads to the cylinder chamber 50 of the cylinder housing 38, and which exits from the cylinder housing 38 in the form of a conduit connector 52. The conduit connector 52, with sealing by means of an O-Ring 53, is inserted into a compressed air connector opening 54 of a medical or dental handpiece 17b. The compressed air connector opening 54 is in communication with a compressed-air supply conduit located in the treatment handpiece 17b, for example, for the formation of a spray or for the drive of a turbine, which in the present instance concurrently forms the compressed-air control conduit 29 for the on-off valve 15. In addition to the conduit connector 52, the cylinder housing 38 possesses a plug-like blind connector 55 for the closing of a water connector aperture 56 which is already present in the handpiece 17b and serving, for example, for the formation of a spray. The blind connector 55 concurrently serves for the improved fastening of the cylinder housing 38 on the treatment handpiece 17b.

In an embodiment pursuant to FIGS. 7 through 9 the clamping valve which forms the on-off valve 15 possesses a clamping lever 57 which acts on the dispensing conduit 4 constituted of elastic material in the sense of effecting the closure thereof. Hereby, the clamping lever 57 is formed by the depressing lever of a foot actuator 58 and is pivotable about the axis C in the sense of the arrows ascertainable in FIG. 1. Furthermore, the clamping lever 57 is constructed as a two-arm lever wherein the one arm forms a depressing arm 59 and the other arms forms a clamping arm 60. The clamping arm 60 extends above the dispensing conduit 4 which is arranged on a clamping abutment 61, whereby the depressing arm 59 stands under the effect of a spring 62 which moves the clamping arm 60 into the clamping position.

The clamping abutment 61 is arranged in the housing of the foot actuator 58, through which there extends the dispensing conduit 4 transversely to the clamping arm 60 of the clamping lever 57. Hereby, as with the regulating valve 16, there is also achieved with the on-off valve 15 the dispensing conduit can be constructed continuously from the fluid 3 of the liquid receptable 1 up to its dispensing end 13 as a single piece which is also of advantage with respect to sterilization.

The spring 62 which acts on the depressing arm 59 is constructed as a helical compression spring and is arranged below the depressing arm 59 between the lastmentioned and a base plate 63 of the housing of the foot actuator 58. From FIGS. 7 through 9 there may be further ascertained that provided between the clamping arm 60 and the dispensing conduit 4, is a clamping element 65 equipped with a clamping bar 64 extending transverse of the conduit 4 and which is movable up and down with the clamping arm 60. For this purpose, the clamping element 65 is fastened to the lower side of the clamping arm 60, referred to in FIG. 9. The on-off valve 15 illustrated in FIGS. 7 through 9 is so constructed that the clamping lever 57 upon sequentially following depression of the pressure arm 59 under the respective release will act alternatingly upon the dispensing conduit 4 in the sense of a closing clamping and of an opening thereof, and namely for so long until a renewed depression is effected. Hereby the clamping lever 57 is in operative connection with a self-actuating, resilient on-and-off latching member 66, which upon a depression of the depression arm 59 at a closed dispensing conduit 4 will engage in a latching pin 67 of the depression arm 59 of the clamping lever 57 and opens the dispensing conduit 4 and retains the latter in the open position, and upon the subsequent depression disengages from the clamping lever so that, thereafter, the depression arm 59 will move upwardly under the effect of the spring 62 and the clamping arm 57 with the clamping together of the dispensing conduit 4 will move downwardly into the clamping or the closed position.

The in-and-out latch 66 is known per se and can operate, for example, as does the illustrated mechanical latch shown in German Laid-open Patent Applications Nos. 19 14 914 and 24 01 576. The in-and-out latching member 66 is shaped in the form of a flat hook which at its one end is pivotable about an axis D and supported on a projection 68 of the base plate 63. Under the effect of a not herein illustrated spring, the in-and-out latching member 66 seeks to effect a rotation about the axis D in a clockwise direction. However, it lies against a locking pin 69.

When one presses down on the depressing arm 59, then the latching pin 67 will slide above the inclined hook end of the in-and-out latching member 66 and engages into the latching opening 17 of the latch 66. When there again is exerted pressure on the depressing arm 59, then the latching pin 67 slides through the pivoting of latch 66 into a position below the contact surface 71 which projects at an incline from the plane of the latch 66. After the release of the depressing arm 59, the latching pin 67 slides out of the plane of the contact surface 71 which projects at an incline from the plane of the latch 66 and bends the latch 66 at its hook and elastically out of its plane. Thereby the latching pin 67 moves below the hook end of the latch 66 so as to move further into the prescribed position shown in FIG. 7.

What is claimed is:

1. An arrangement for the conveyance of a sterile liquid to a medical handpiece (17), supplied by means of a supply hose (19), in which the sterile liquid is ejected under pressure from a dispensing end of an elastic hose dispensing conduit (4) at the head of the handpiece (17), wherein the dispensing conduit (4) is provided with a clamping regulating valve (16) in proximity to the handpiece (17), for adjustment of its throughflow rate and wherein the handpiece (17) contains a compressed air conduit (29), for example for driving a turbine motor or for the formation of a spray, which is controlled by a valve in the supply hose (19), characterized in that said clamping regulating valve (16) is connected downstream to an on/off clamping valve (15) acting on said elastic dispensing conduit (4) which is connected through a bypass conduit (51) to said compressed air conduit (29), said on/off clamping valve (15) comprising a piston (39) arranged in a cylinder (38), and wherein both said clamping valves (15,16) function by clamping said elastic hose dispensing conduit (4) and are combined in a valve arrangement (14) located in proximity to the connection of the supply hose (19) to the handpiece (17) and are detachably connected thereto.

2. Arrangement according to claim 1, characterized in that said on/off clamping valve (15) includes a piston (39) movable in a cylinder housing (38) and functioning to clamp said elastic dispensing conduit (4), one side of said piston (39) being biased against at least one spring (40) by compressed air from the compressed air control conduit (29) such that when the compressed air is turned off, the piston (39) is biased by the spring (40) to clamp the elastic dispensing conduit (4) to effect closing thereof.

3. Arrangement according to claim 2, characterized in that said piston (39) includes a throughbore (41) extending transversely to its direction of movement, through which said elastic dispensing conduit (4) extends through inlet and outlet apertures (42,43) in the wall of the cylinder housing (38), and wherein on the pressurized air side of the piston (39) there is arranged a fixed clamping pin (44) in the cylinder housing (38), which extends through an aperture (45) of the piston (39) into the throughbore (41) and serves as a clamping abutment during closure of the elastic dispensing conduit (4).

4. Arrangement according to claim 3, characterized in that ballbearings (46) are supported in apertures (45) in the piston (39) in contact against said clamping pin (44).

5. Arrangement according to claim 2 or 3 or 4, characterized in that said spring (40) is a compression spring arranged on one side of the piston 39 opposite to the compressed air side thereof.

* * * * *